United States Patent [19]
Adusumilli et al.

[11] Patent Number: 5,919,491
[45] Date of Patent: Jul. 6, 1999

[54] METHOD AND COMPOSITION FOR INCREASING CALCIUM UPTAKE

[75] Inventors: Prasad S. Adusumilli, Edison; Vimala Sivapragasam, Parsippany, both of N.J.

[73] Assignee: SmithKline Beecham Corporation, Philadelphia, Pa.

[21] Appl. No.: 08/522,377

[22] PCT Filed: May 12, 1995

[86] PCT No.: PCT/US95/06239

§ 371 Date: Nov. 12, 1996

§ 102(e) Date: Nov. 12, 1996

[87] PCT Pub. No.: WO95/01186

PCT Pub. Date: Nov. 23, 1995

[51] Int. Cl.⁶ .......................... A61K 33/14; A61K 33/06; A61K 33/10; A61K 33/08
[52] U.S. Cl. .......................... 424/678; 424/682; 424/687; 424/693; 424/696
[58] Field of Search .................... 424/687, 678, 424/693, 696, 682

[56] References Cited

U.S. PATENT DOCUMENTS

| | | |
|---|---|---|
| 4,163,777 | 8/1979 | Mitra .......................... 424/21 |
| 4,744,987 | 5/1988 | Mehra et al. .................. 424/156 |
| 4,752,479 | 6/1988 | Briggs et al. .................. 424/472 |
| 4,814,177 | 3/1989 | Walsdorf et al. ................ 424/464 |
| 4,886,669 | 12/1989 | Ventouras .................... 424/469 |
| 5,007,790 | 4/1991 | Shell . | |
| 5,132,116 | 7/1992 | Sournac et al. . | |
| 5,582,837 | 12/1996 | Shell .......................... 424/451 |

*Primary Examiner*—Raymond Henley, III
*Attorney, Agent, or Firm*—Dara L. Dinner; Stephen Venetianer; Charles M. Kinzig

[57] ABSTRACT

This invention relates to a hydrophilic matrix containing a pharmaceutically acceptable calcium source for use as a calcium supplement for mammals.

15 Claims, 6 Drawing Sheets

METHOD AND COMPOSITION FOR INCREASING CALCIUM UPTAKE

This application is a 371 of PCT/US95/06239 filed May 12, 1995.

SCOPE OF THE INVENTION

This invention relates to a hydrophilic matrix containing a pharmaceutically acceptable calcium source for use as a calcium supplement for mammals.

BACKGROUND OF THE INVENTION

Calcium supplements are widely used for the treatment of osteoporosis. The bioavailability of these preparations are relatively low. This problem has been noted by a number of medical professionals recently as the issue of osteroporosis in an aging population is becoming a well publicized issue (F-D-C-Reports—"The Tan Sheet", Mar. 14, 1994). Not all calcium supplements are the same. Bioavailability appears to differ among and between sources of calcium. It often is influenced by manufacturing processes. Solubility in vitro is not necessarily correlated with bioavailability. And even though the same total amount of calcium is ingested, more calcium may be absorbed if the supplement is taken in multiple small doses, especially when taken with food, that when taken in just a few large doses. Other nutritional depravations, such as inadequate vitamin D intake, may influence calcium absorption. What ever the reason, calcium absorption from supplements can be quite variable from preparation to preparation and is not a particularly efficient process vis-a-vis the currently available oral supplements.

Adequate calcium intake whether from food or supplements is important in both preventive and treatment regimens for osteoporosis and osteomalacia. The use of calcium supplements has increased dramatically in recent years. Some recent evidence indicates that calcium intake may be associated with a reduced risk of colon cancer and may have a blood-pressure lowering effect. If these initial results are verified it will likely further increase the use of calcium supplements, making it more important that optimal dosing regimens be developed to minimize toxicity and maximize their efficacy (J. Blanchard and J. M. Aeschlimann. Calcium Absorption in Man: Some Dosing Recommendations. J. Pharmacokinetics and Biopharmaceutics, 17(6), 1989, 631–644). Concern has been expressed that the bioavailability of calcium from many calcium carbonate supplements is low. For most commercially available products, calcium absorption in adults commonly averages 25–35% of the available calcium in the dosage form. The low bioavailability could be attributed to either an incomplete drug release or to a too short residence time of the pharmaceutical dosage form in the absorption section of the GI Tract (H. M. Ingani, et al. Conception and in vivo investigation of peroral sustained release floating dosage forms with enhanced gastrointestinal transit. Int. J. Pharm., 35 (1987) 157–164). Therefore, design of better delivery systems seem to be necessary. Some researchers have shown that the absorption of calcium involves a saturable (active) and a nonsaturable (passive) component. The combination of the acidic pH and calcium binding protein in the duodenum and upper jejunum makes the absorption of calcium much greater in the duodenojejunal section (Lindsay H. Allen. Calcium bioavailability and absorption: a review. Am J Clin Nutr., 1982; 35;783–808). The work of several other investigators indicate that an inverse relationship exists between calcium intake and absorption efficiency. The division of the daily dose into equal increments taken at equally spaced interval over the course of the day is recommended as a useful procedure for increasing the absorption efficiency and efficacy. In addition, it is reported that single unit systems can be retained in the stomach for long periods (10 hours and longer) if administered after a heavy meal (R. Malagelada et al. The stomach, but not small bowel, discriminates between solid and liquids in man. Gastroenterology, 84 (1983) 1237).

Previous studies aimed at increasing calcium uptake in the intestine have mainly concentrated on increasing the dissolution rate and increasing the solubility of the calcium source. Based on this information, controlled release calcium oral dosage forms with increased gastric retention time seem to be appropriate to increase the bioavailability.

To achieve this goal a hydrophilic matrix system was used to encapsulate a source of calcium ion, such as for example calcium carbonate. The test matrix material was different grades of hydroxypropylmethylcellulose (HPMC). The grades of HPMC represent a variety of polymers with different molecular weights. Methocel K100LV and K4M were selected. It is reported that these polymers demonstrate floating and swelling behavior. [V. S. Gerogiannis, et al., Floating and swelling characteristics of various excipients used in controlled release technology, Drug Dev. Ind. Pharm., 19(9), 1061–1081 (1993)].

SUMMARY OF THE INVENTION

This invention relates to a process for increasing calcium absorption in a mammal which process comprises forming a matrix around a pharmaceutically acceptable solid calcium source wherein the matrix-forming material comprises a hydrophilic polymer.

In a further aspect, this invention relates to an improved pharmaceutically acceptable oral preparation containing a source of calcium in solid form wherein the improvement comprises surrounding said calcium source in a hydrophilic polymer matrix to increase retention in the stomach.

In yet a further aspect, this invention comprises a method for increasing calcium absorption in a mammal which method comprises administering to a mammal in need of a calcium supplement a pharmaceutically acceptable solid dosage form containing a source of calcium entrapped in a hydrophilic matrix which results in increased retention of the matrix material in the stomach.

DETAILED DESCRIPTION OF THE INVENTION

Figure 1:
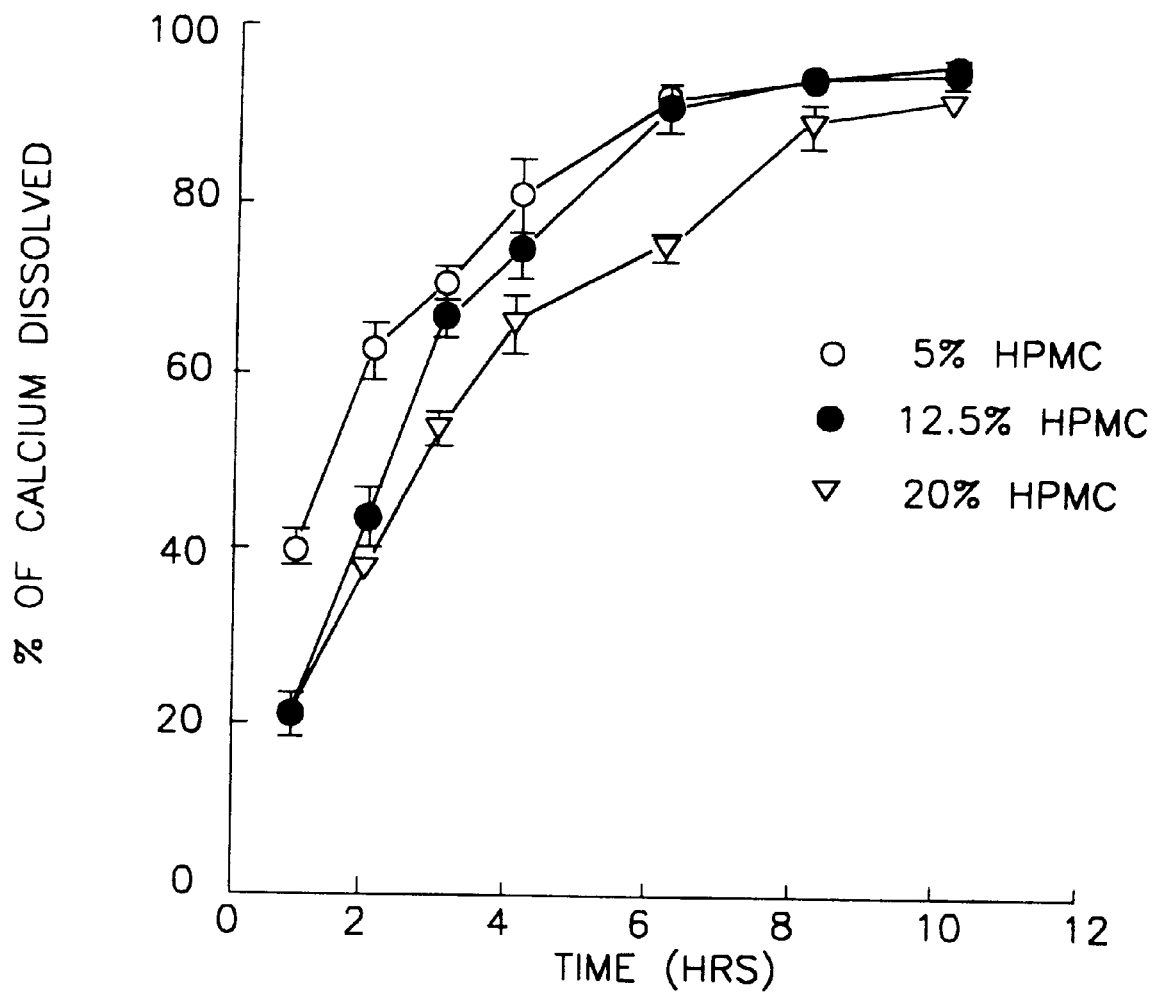
FIG. 1 shows graphic data of calcium released from HPMC at three concentration levels (viscosity grade: 100 cps).

In its broadest aspect, this invention provides a means for increasing the gastric uptake of calcium in a mammal from a calcium supplement by the expedient of forming a matrix around the calcium material with a hydrophilic polymer and confecting that material into an oral dosage form. It has been found that the hydrophilic material forming matrix swells in water and as a result prolongs the gastric residence time and/or prevents erratic gastric emptying during the digestive phase. Consequently the calcium source enjoys a longer residence time in the upper intestine thereby enhancing the amount of calcium which can be absorbed.

These formulations and processes are concerned only with solid or viscous, oral dosage forms. Tablets or chewable troches or lozenges are of most interest herein. And this technology will have the most successful application in these types of preparations. As for the makeup of the product, it will comprise a calcium source entrapped in a matrix of hydrophilic polymer, this complex being formulated into a tablet, troche, lozenge or the like using conventional methods and conventional excipients.

The calcium source which can be used in this invention is any pharmaceutically acceptable calcium salt or chelated calcium product. The following exemplary calcium products have been used in supplements: calcium carbonate, calcium phosphate, calcium citrate, calcium gluconate, calcium oxalate, and glycine calcium. Other forms of calcium can also be used, provided they are acceptable for human use.

Hydrophilic matrix forming polymers are used to coat the calcium source. These polymers will be non-toxic, that is safe for human consumption when administered orally. One useful example of such polymers is the celluloses, particularly hydroxypropyl methyl cellulose (HPMC). This polymer and the group of polymers of like nature provide two benefits: i) the matrix they form with the calcium source effects a sustained release preparation, and ii) when exposed to water the polymers demonstrate a swelling and floating behavior. Both characteristics contribute to a longer residence time in the GI tract. Longer term exposure contributes to more calcium being absorbed by the gut.

Tablets, troches, lozenges and the like can be prepared using standard practices and procedures. Excipients can be selected from any of the know, pharmaceutically acceptable materials currently used or known for making said tablets, etc. See for example *Remington's Pharmaceutical Sciences*, A. R. Gennaro Ed., 18th Edition, Mack Publishing Co., Easton, Pa., USA (1990) and similar reference works.

Other components can be added into these preparations. For example an antacid can be added to neutralize stomach acid. Or a drug associated with bone mineral resorption or one which enhances calcium uptake, for example, might be added into the formulation. Flavoring agents, colors-imparting agents, preservatives, etc., can be included as well.

The following examples are set out as a means of illustrating the invention. They are not intended to limit the invention and should not be interpreted to do so. Reference is made to the claims for what is reserved to the inventors hereunder.

EXAMPLES

Example I

Preparation of Tablets

A dry blend consisting of calcium carbonate (2 kg) and Methocel E5 (100 mg, 5% of calcium carbonate) was mixed in a bowl mixer (Hobart Mixer) for 5 min. Approximately 360 ml of distilled water was added gradually to form a wet granulation, which was then dried overnight in an oven set at 40° C. The dry granules were screened through a 20 mesh sieve and stored as stock granules. This granulation was then mixed with different percentages of Methocel K100LV and/or K4M as per Table I below for 20 min. Finally 2.5% of stearic acid and 0.5% of sipernat were added and mixed for another 5 min. in a V-blender. The blend so obtained was compressed into tablets using a Stokes single punch press (Key Industrials Inc., Englishtown, N.J.) to make the tablets. The average hardness for all formulations were adjusted to 14.6–17.2 scu and the weight variation of all nine formulations were within 10% of the target weights. The elemental calcium in each tablet is approximately 250 mg.

Experimental Design

Nine formulations were generated using a $3^2$ full factorial design. Using different levels and grades of HPMC, the viscosity and concentration of HPMC in tablets were optimized to achieve the desired in vitro dissolution profile. Independent variables used in the design were viscosity of the polymeric system and concentration of the polymer system in the dosage form. Viscosity and concentration were allowed to vary from 100 cps (−1) to 4000 cps (1) and 5% HPMC (−1) to 20% (1), respectively. Percent of calcium dissolved at 1, 2, 3, 4, 6, 8 and 10 hours were used as the dependent variables. The experimental design is given below in Table 1.

TABLE 1

| Exp. Number | Controled Factors | |
|---|---|---|
| | Viscosity | Concentration |
| 1 | −1 | −1 |
| 2 | −1 | 0 |
| 3 | −1 | 1 |
| 4 | 0 | −1 |
| 5 | 0 | 0 |
| 6 | 0 | 1 |
| 7 | 1 | −1 |
| 8 | 1 | 0 |
| 9 | 1 | 1 |

The viscosity of Methocel K100LV is 100 cps while Methocel K4M is 4000 cps. Eighth root equation (METHOCEL Cellulose Ethers Technical Handbook, Dow Chemical U.S.A. Midland, Mich.) was employed to calculate the correct blend needed to yield the intermediate viscosity.

Dissolution of the nine formulations was measured using USP apparatus 1 (Vanderkamp 600 dissolution apparatus, Van-Kel Industries, Edison, N.J.) at 100 rpm in 900 ml of 0.1N HCl kept at 37° C. and aliquots (3 ml) of the dissolution medium was withdrawn from each vessel at 1 hour, 2 hours, 3 hours, 4 hours, 6 hours, 8 hours and 10 hours. All samples were filtered through 0.45 μm cellulose acetate membranes, diluted with distilled water and analyzed for dissolved calcium by Atomic Absorption Spectrophotometry (Varian Techtron Pty. Ltd. Springvale, Australia). Percentage of dissolved calcium was calculated by dividing the measured calcium content of a particular sample by the calcium weight of the tablet.

An inverse relationship was found to exist between concentration of the HPMC matrix, viscosity of the HPMC matrix and calcium release rate. Results of the in vitro dissolution tests are shown in table 2.

TABLE 2

|  | Exp. 1 | Exp. 2 | Exp. 3 | Exp. 4 | Exp. 5 | Exp. 6 | Exp. 7 | Exp. 8 | Exp. 9 |
|---|---|---|---|---|---|---|---|---|---|
| Wgt (mg)* | 809.3 | 865.3 | 899.8 | 817.4 | 867.2 | 907.3 | 801.2 | 850.8 | 911.0 |
| Hardness* (scu) | 16.5 | 16.1 | 17.2 | 16.5 | 16.5 | 14.6 | 16.4 | 16.8 | 15.8 |
| % of Ca Release** | | | | | | | | | |
| 1 h | 40.1 | 20.8 | 20.9 | 24.8 | 18.5 | 12.1 | 21.3 | 14.2 | 10.9 |
| 2 h | 63.4 | 43.9 | 38.2 | 36.4 | 32.9 | 20.4 | 32.6 | 23.0 | 17.3 |
| 3 h | 71.4 | 67.4 | 54.9 | 53.2 | 45.8 | 28.7 | 45.3 | 33.1 | 25.0 |
| 4 h | 81.5 | 75.5 | 67.5 | 67.8 | 58.1 | 39.5 | 58 | 40.6 | 29.9 |
| 6 h | 92.7 | 91.8 | 76.6 | 86.7 | 76.4 | 58.8 | 82.6 | 71.1 | 40.7 |
| 8 h | 95.2 | 95.5 | 90.5 | 93.8 | 90.5 | 82.6 | 91.3 | 82.6 | 52.7 |
| 10 h | 97.3 | 96.4 | 93.3 | 97.0 | 93.5 | 87.9 | 95.4 | 91.4 | 63.0 |

*The weight and hardness are the average of ten tablets.
**The percentage of calcium dissolved is the mean of four tablets.

Figure 2:
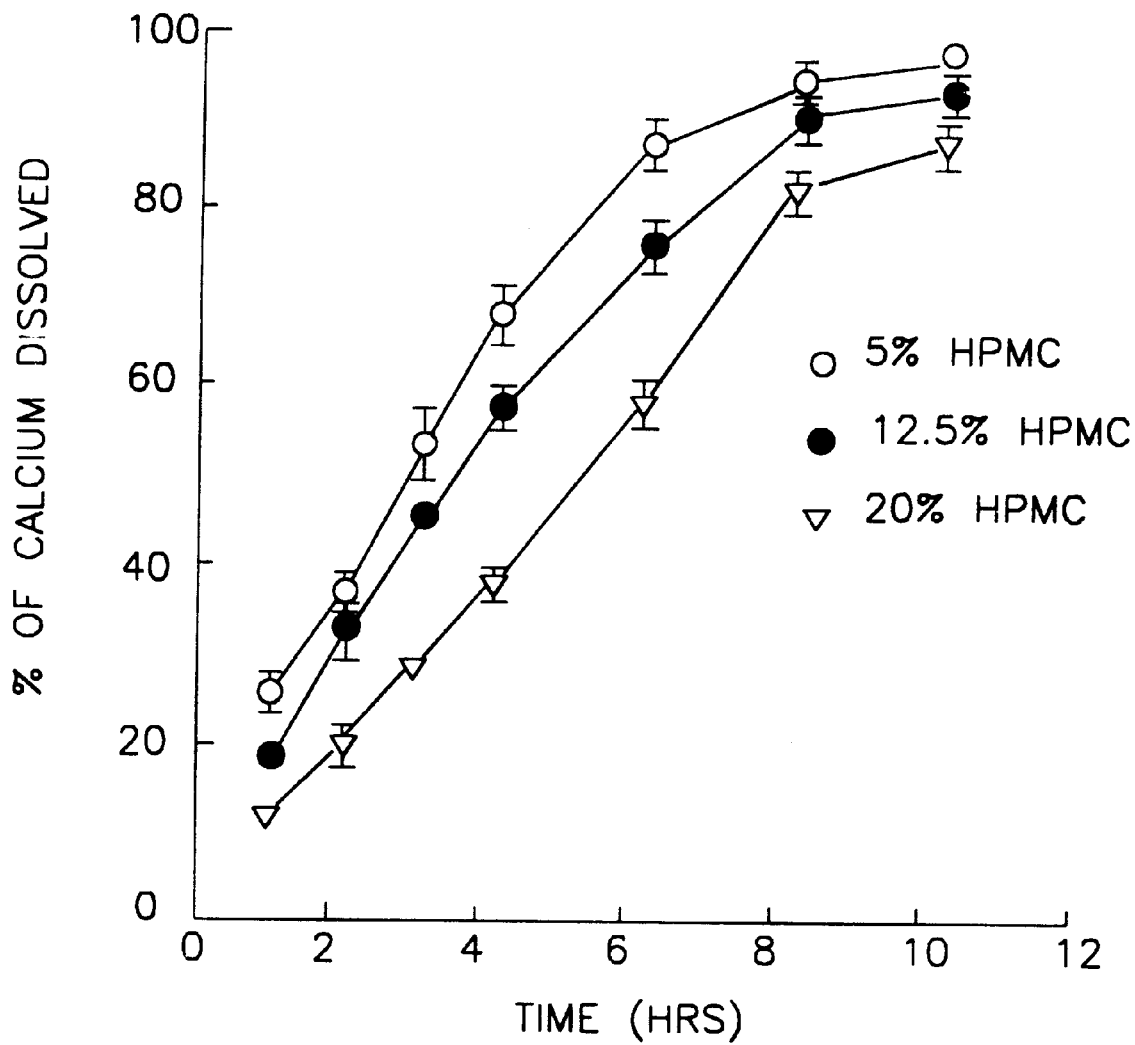
FIG. 2 shows graphic data of calcium released from HPMC at three concentration levels (viscosity grade 2050 cps).
Figure 3:
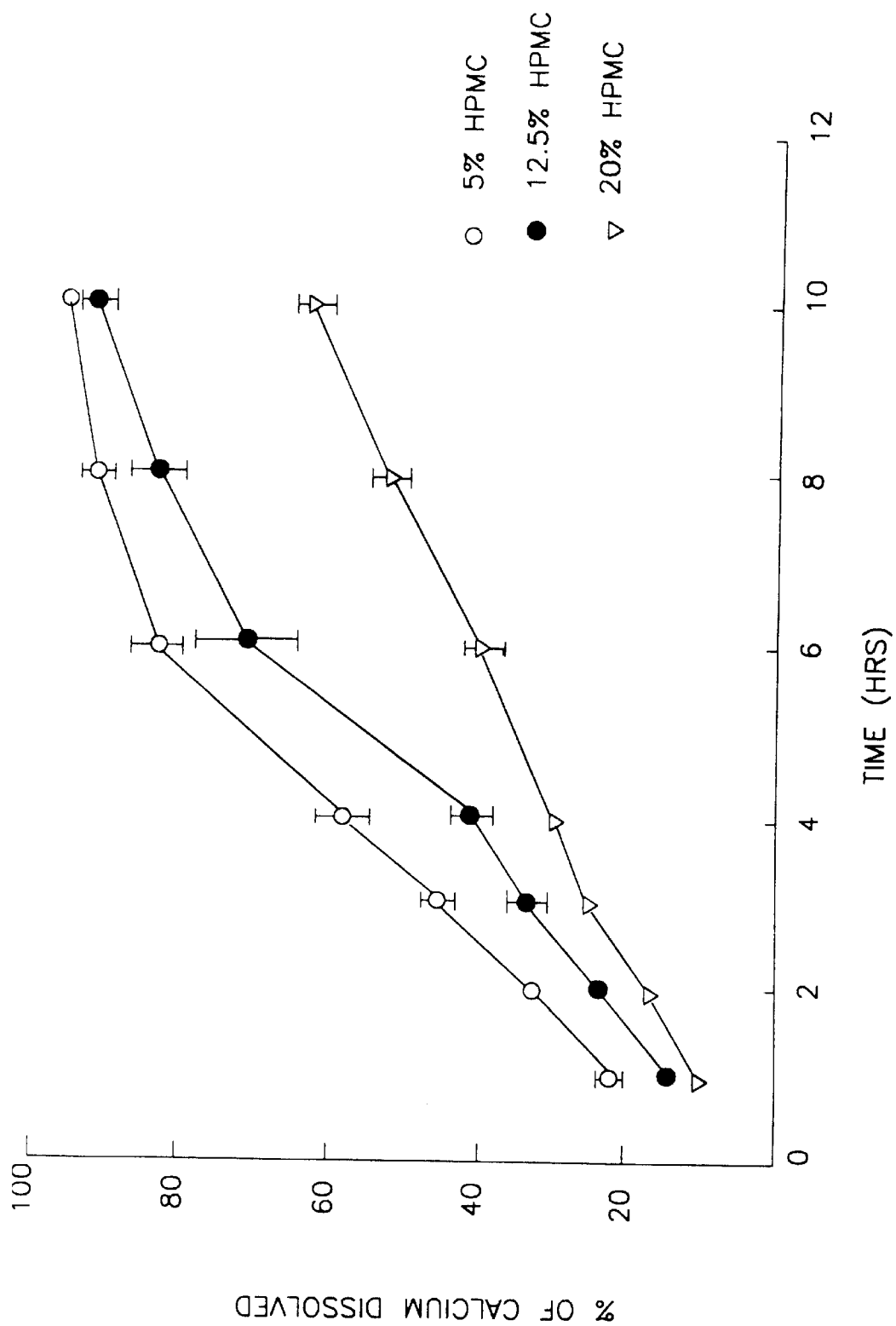
FIG. 3 shows graphic data of calcium released from HPMC at three concentration levels (viscosity grade: 4000 cps).
Figure 4:
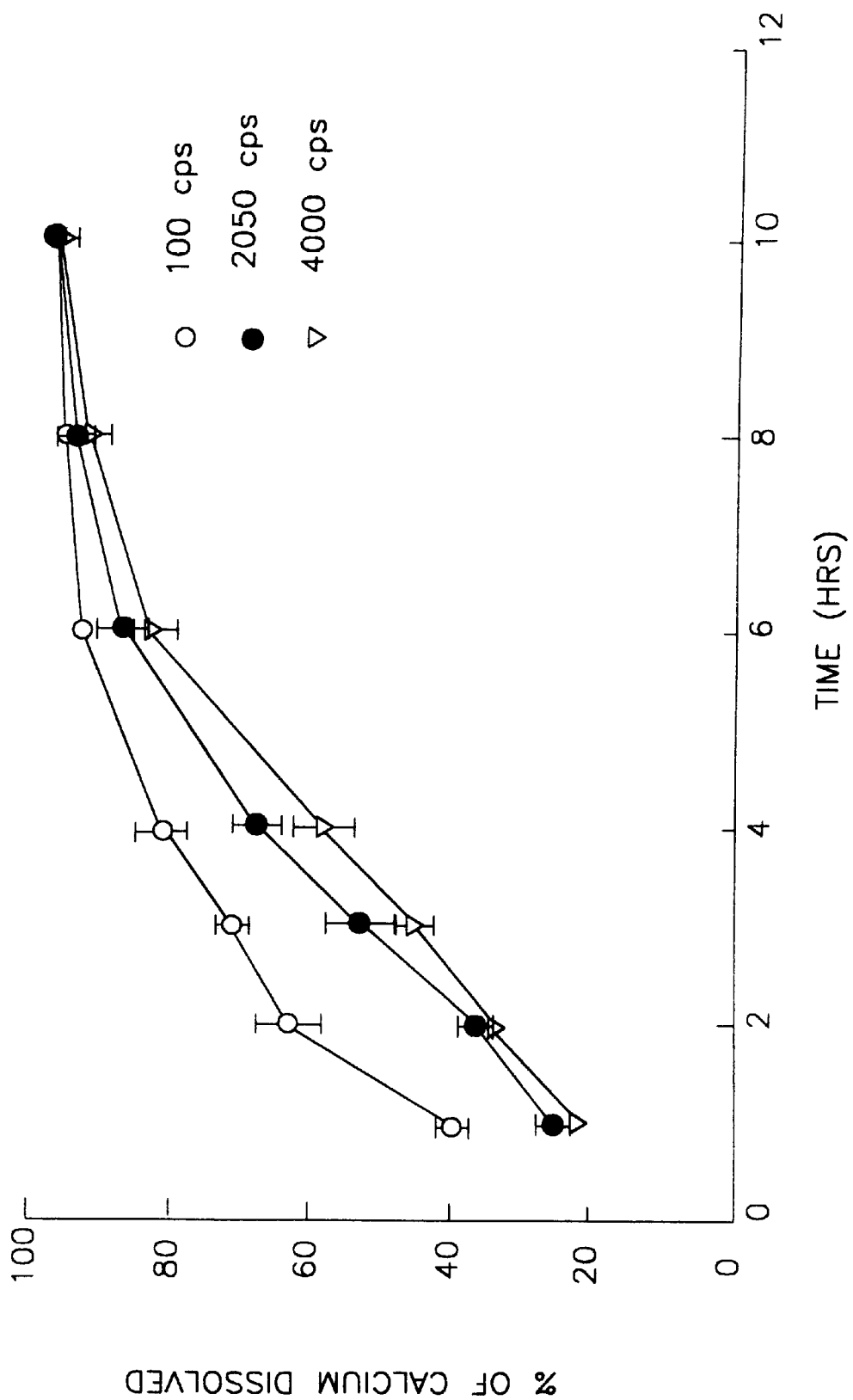
FIG. 4 shows graphic data of calcium released from HPMC at three viscosity grades (5% HPMC).
Figure 5:
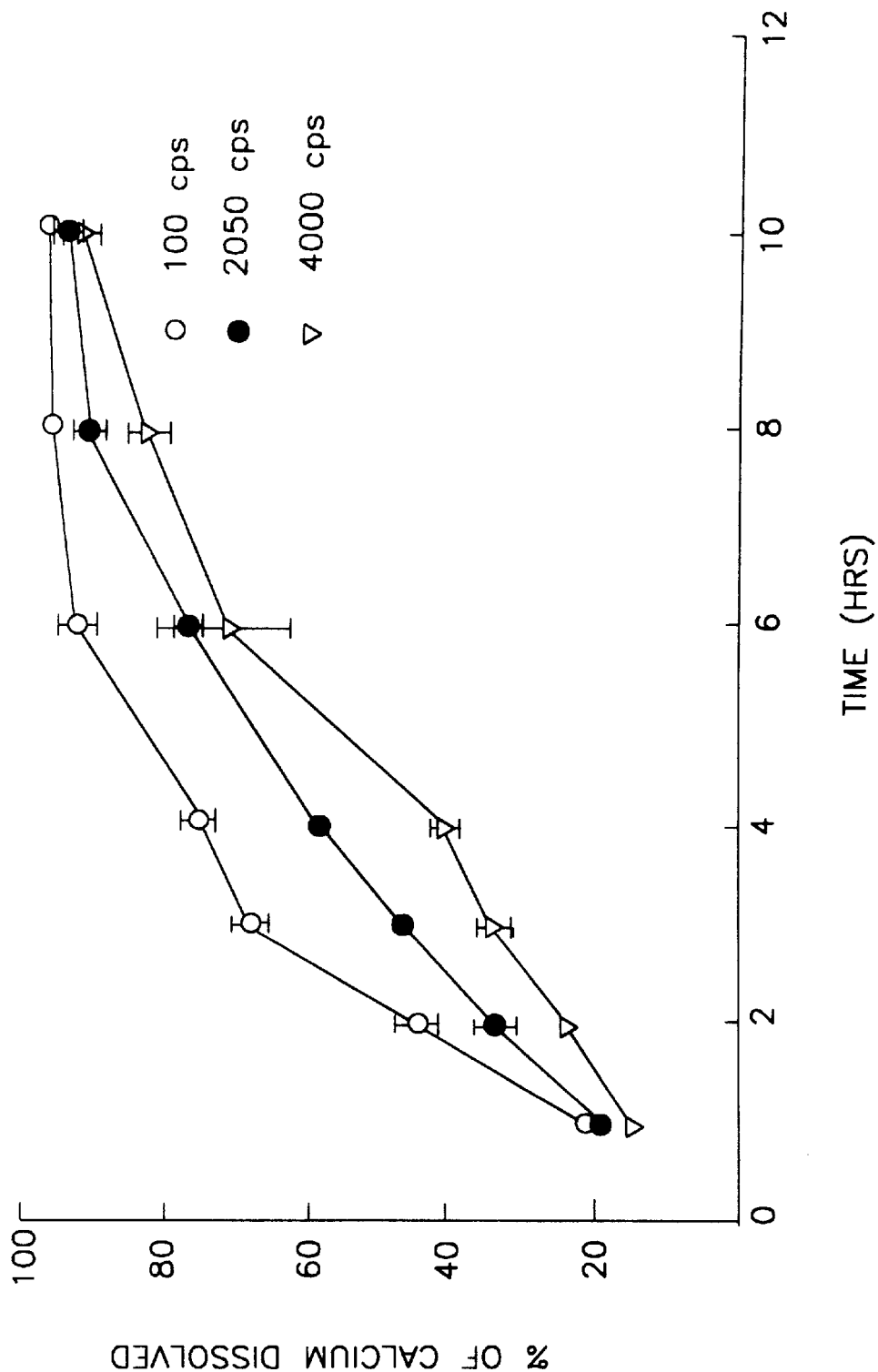
FIG. 5 shows graphic data of calcium released from HPMC at three viscosity grades (12.5% HPMC).
Figure 6:
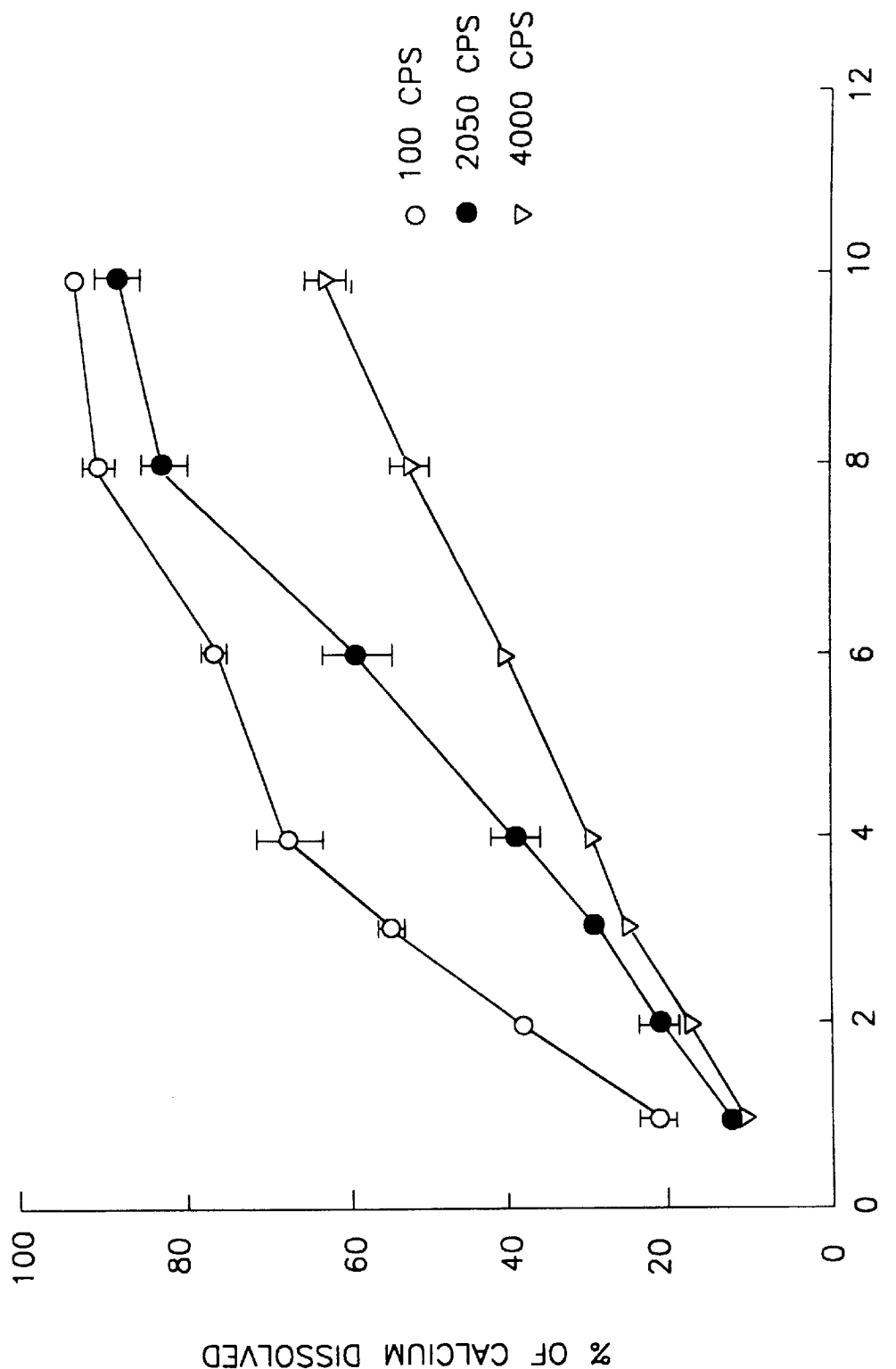
FIG. 6 shows graphic data of calcium released from HPMC at three viscosity grades (20% HPMC).

The effect of viscosity of the polymeric systems is illustrated in FIG. 1, FIG. 2 and FIG. 3, and the effect of concentration in FIG. 4, FIG. 5 and FIG. 6. It can be seen that there is a fairly wide range of dissolution among the nine formulations. There are only two formulations that average over 90% at 6 hours. 5% K100LV (100 cps) has a dissolution of 92.7±1.42 (mean±1 SD, n=4) while 12.5% K100LV, 100 cps has a dissolution of 91.8%±2.83.

Methocel K4M, 20%, (4000 cps) gave the lowest dissolution, releasing only about 40.7% of the calcium by 6 hours. All other formulations had an intermediate dissolution ranging from 58.8% to 86.6%. It can also be seen that in all formulations an inverse relationship exists between concentration of the HPMC matrix, viscosity of the HPMC matrix and calcium release rate. The higher the concentration and viscosity, the lower the calcium release rate.

What is claimed is:

1. A method of increasing calcium absorption in a mammal in need thereof, which method comprises administering to said mammal a pharmaceutically acceptable calcium ion source which is encapsulated with a hydrophilic matrix polymer.

2. The method according to claim 1 wherein the hydrophilic polymer is hydroxypropylmethylcellulose of varying molecular weight.

3. The method according to claim 2 wherein the hydroxypropylmethylcellose is composed of one or more different viscosity grades.

4. The method according to claim 3 wherein the viscosity grades of the hydroxypropylmethylcellulose are individually 100 cps, 2500 cps and 4000 cps.

5. The method according to claim 2 wherein the calcium ion source is calcium carbonate.

6. The method according to claim 1 wherein the hydrophilic polymer is hydroxypropylmethylcellulose having a viscosity grade of 100 cps.

7. The method according to claim 1 wherein the hydrophilic polymer is hydroxypropylmethylcellulose having a viscosity grade of 2500 cps.

8. The method according to claim 1 wherein the hydrophilic polymer is hydroxypropylmethylcellulose having a viscosity grade of 4000 cps.

9. The method according to any of claims 1, 6, 7, or 8 wherein the calcium ion source is calcium carbonate.

10. A method for increasing calcium absorption in a mammal which method comprises administering to a mammal in need of a calcium supplement a pharmaceutically acceptable solid dosage form containing a source of calcium entrapped in a hydrophilic matrix which results in increased retention of the matrix material in the stomach.

11. The method according to claim 10 wherein the calcium source is calcium carbonate.

12. The method according to claim 11 wherein the hydrophilic matrix is composed of a hydrophilic polymer which is hydroxypropylmethylcellulose.

13. The method according to claim 12 wherein the hydroxypropylmethylcellulose has a viscosity grade of 100 cps.

14. The method according to claim 12 wherein the hydroxypropylmethylcellulose has a viscosity grade of 2500 cps.

15. The method according to claim 12 wherein the hydroxypropylmethylcellulose has a viscosity grade of 4000 cps.

* * * * *